(12) United States Patent
Frippiat et al.

(10) Patent No.: US 7,812,004 B2
(45) Date of Patent: Oct. 12, 2010

(54) INULIN PRODUCTS WITH IMPROVED NUTRITIONAL PROPERTIES

(75) Inventors: Anne Frippiat, Sterrebeek (BE); Jan Van Loo, Agatha Rode (BE); Georges Smits, Gijzegem-Aalst (BE)

(73) Assignee: Tiense Suikerraffinaderij N.V. (BE)

( * ) Notice: Subject to any disclaimer, the term of this patent is extended or adjusted under 35 U.S.C. 154(b) by 2360 days.

(21) Appl. No.: 10/182,064

(22) PCT Filed: Feb. 14, 2001

(86) PCT No.: PCT/EP01/01600

§ 371 (c)(1),
(2), (4) Date: Jul. 24, 2002

(87) PCT Pub. No.: WO01/60176

PCT Pub. Date: Aug. 23, 2001

(65) Prior Publication Data

US 2003/0068429 A1   Apr. 10, 2003

(30) Foreign Application Priority Data

Feb. 15, 2000   (EP) .................................. 00103056

(51) Int. Cl.
*A61K 31/733*   (2006.01)
*C07H 3/06*   (2006.01)
*C08B 37/18*   (2006.01)
*C12P 19/02*   (2006.01)

(52) U.S. Cl. ..................................... 514/54; 536/123.1

(58) Field of Classification Search ................... 514/23, 514/54; 536/128, 123.12, 127, 124; 426/658
See application file for complete search history.

(56) References Cited

U.S. PATENT DOCUMENTS 5,527,556 A * 6/1996 Frippiat et al. ............... 426/573
6,303,778 B1 * 10/2001 Smits et al. .................. 536/128
6,489,310 B1 * 12/2002 Brassart et al. ............... 514/54

FOREIGN PATENT DOCUMENTS

| WO | WO 93/02566 | 2/1993 |
| WO | WO 96/01849 | 1/1996 |
| WO | WO 96/03888 | 2/1996 |
| WO | 98/52578 | 11/1998 |
| WO | 99/59600 | 11/1999 |

OTHER PUBLICATIONS

Andersen et al., "An enzymatic method for the determination of fructans in foods and food products", Danish Veterinary and Food Administration, Institute of Food Research and Nutrition, Apr. 23, 1999, Eur Food Res Technol (1999), pp. 148-152.
Reddy et al., "Effect of dietary oligofructose and inulin on colonic preneoplastic aberrant crypt foci Inhibition,", Carcinogenesis, vol. 18, No. 7, pp. 1371-1374 (1997).
Taper et al., "Influence of Inulin and Oligofructose on Breast Cancer and Tumor Growth", American Society for Nutritional Sciences, 1999, pp. 1488-1491.
Van Bekkum et al., "Carbohydrates as Organic Raw Materials III", Developed from a Workshop organized by the Carbohydrate Research Foundation, Wageningen, The Netherlands, Nov. 28-29, 1994.
Delzenne, et al., "Effect of Fermentable Fructo-Oligosaccharides on Mineral, Nitrogen and Energy Digestive Balance in the Rat", Life Sciences, vol. 57, No. 17, pp. 1579-1587, 1995.
Van Loo et al., "On the Presence of Inulin and Oligofructose as Natural Ingredients in the Western Diet", Critical Reviews in Food Science and Nutrition, 35(6): pp. 525-552 (1995).

* cited by examiner

*Primary Examiner*—Eric S Olson
(74) *Attorney, Agent, or Firm*—Hayes Soloway P.C.

(57) ABSTRACT

The invention relates to novel inulin products and compositions thereof, to their manufacture, to their use for modifying and modulating the bacterial flora and the fermentation pattern of inulin in the large intestine of humans, mammals or other vertebrates, to their use for providing improved inulin-associated nutritional effects/benefits, as well as to their use for the manufacture of consumer products and compositions for providing said effects/benefits in healthy, disfunctioned and diseased humans, mammals and other vertebrates.

Figure 1:
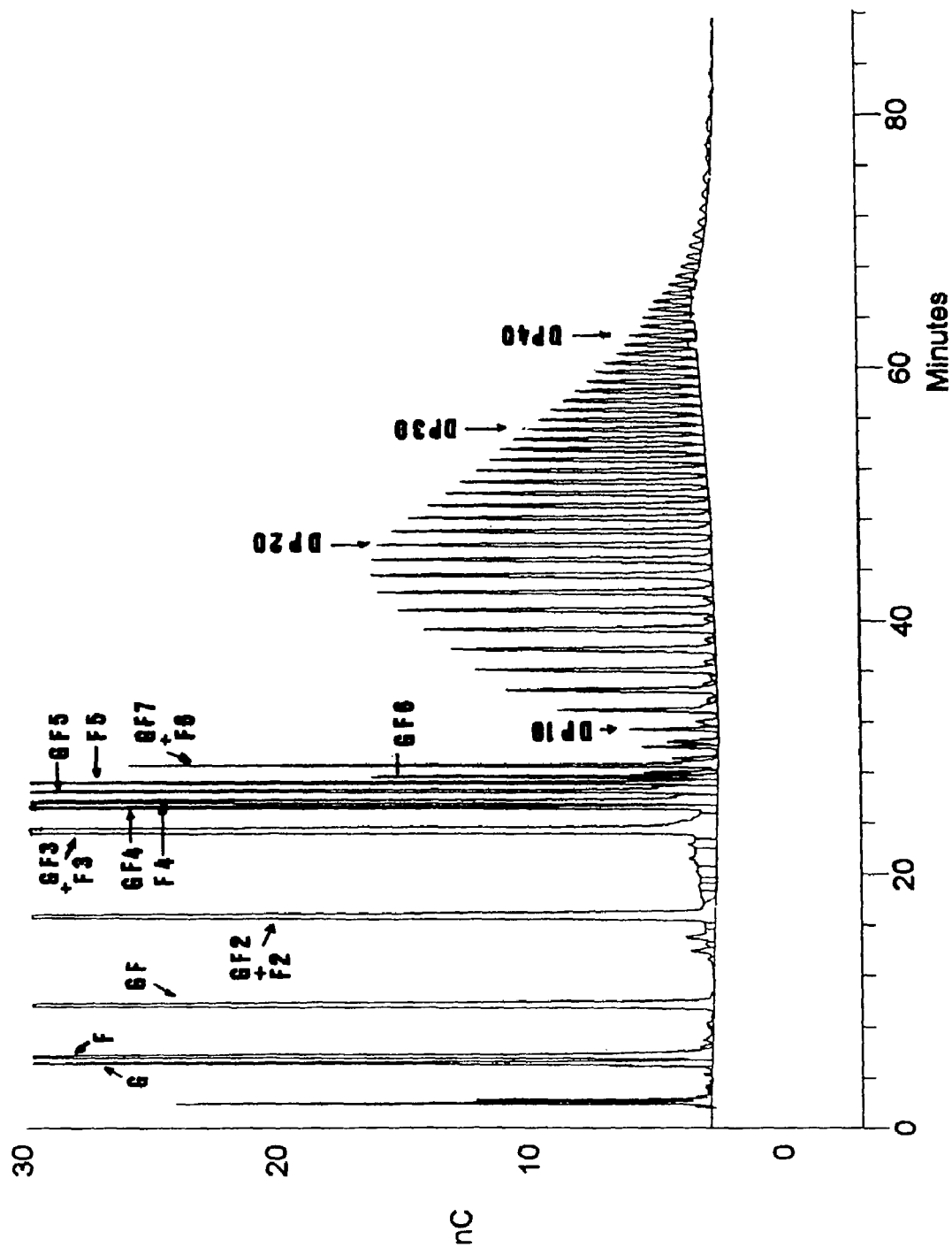

The novel inulin products consist of a particular mixture of an easily fermentable inulin (EFI) component and a hardly fermentable inulin (HFI) component.

The nutritional effects/benefits include dietary fiber effects, improved mineral absorption, particularly calcium and magnesium, bone mineral density increase, reduction of bone mineral density loss, modulation of lipid metabolism, stimulation of the immune system, and anti-cancer effects. The novel inulin products are particularly suitable for the manufacture of a composition or a medicament for preventing, for postponing and/or for treating osteoporosis in humans, particularly in post-menopausal women and elderly people.

21 Claims, 1 Drawing Sheet

INULIN PRODUCTS WITH IMPROVED NUTRITIONAL PROPERTIES

CROSS REFERENCE TO REFATED APPLICATIONS

This application is a 371 of PCT/EP01/01600, filed Feb. 14, 2001, and claims priority to European Patent Application (EPO) 00103056.8, filed Feb. 15, 2000.

FIELD OF THE INVENTION

This invention relates to novel inulin products and compositions thereof, to their manufacture and to their use for modifying and modulating the bacterial flora composition and the fermentation pattern of inulin in the large intestine of humans, mammals and other vertebrates, to their use for providing improved inulin-associated nutritional effects/benefits, and to their use for the manufacture of a composition, a consumer product, a pharmaceutical or a medicament for providing said effects/benefits in humans, mammals and other vertebrates.

PRIOR ART AND TECHNOLOGICAL BACKGROUND

Inulin is a fructan-type carbohydrate, consisting mostly of fructose units, which occurs in many plants as a reserve carbohydrate. Inulin can be produced by certain bacteria and can also be enzymatically produced in vitro from sucrose. Inulin naturally occurs as a polydisperse mixture of carbohydrate molecules which are essentially composed of fructosyl units forming chains in which the fructosyl units are mainly or exclusively linked to one another by a β(2,1) bound. The mainly linear chains are possibly bearing one or more side chains essentially composed of fructosyl units, thus forming branched inulin molecules with a fructosyl-fructosyl linkage at the branching point commonly formed by a fructosyl-fructosyl β(2,6) bound. Inulin molecules from plant origin mostly contain one terminal glucosyl unit. Accordingly, inulin molecules can be represented by the formula GFn or Fm wherein G represents a terminal glucosyl unit, F represents a fructosyl unit and n and m represent the number of fructosyl units linked to one another through a β(2,1) and/or a β(2,6) bound. The number n+1, respectively m, indicates the degree of polymerisation (DP) of the inulin molecule. Inulin is further characterised by its (number) average degree of polymerisation, represented by $\overline{DP}$. This is the value which corresponds to the total number of saccharide units (G and F units) in a given inulin sample divided by the total number of inulin molecules in said sample, without taking into account the monosaccharides glucose (G) and fructose (F) and the disaccharide sucrose (GF) which are possibly present in the sample. The average degree of polymerisation ($\overline{DP}$) is commonly determined by the method described by De Leenheer et al. (1).

Native inulin from plant sources (i.e. the inulin as present in the plant) appears as a polydisperse mixture of mainly linear polysaccharide chains with a (DP) ranging from 2 to about 100, whereas inulin molecules from bacterial origin, which commonly are branched ones, usually have much higher (DP) values, even up to about 115.000. Plant inulin has a ($\overline{DP}$) which largely depends on the plant source and on the harvest, storage and processing conditions. Natural (or standard grade) inulin indicates herein inulin which has been extracted from plant sources, purified and isolated, without applying a treatment for reducing or increasing its ($\overline{DP}$) and it usually has a ($\overline{DP}$) which is about 1 unit lower than the ($\overline{DP}$) of the corresponding native inulin.

Inulin molecules with a low degree of polymerisation, usually defined as a (DP)<10, are named inulo-oligosaccharide(s), fructo-oligosaccharide(s) or oligofructose. These terms, including linear and branched inulin of (DP)<10, are commonly, also herein, used interchangeably. Oligofructose is also termed herein short-chain inulin.

Inulin is commonly manufactured from plant sources, mainly from roots of Chicory (*Cichorium intybus*), but also from tubers of Jerusalem artichoke (*Helianthus tuberosus*) and from the piña (head) of the Blue Agave plant, in which inulin can be present in concentrations up to about 20 wt % on fresh plant material (hereinafter wt % means per cent by weight). Inulin can be readily extracted from said plant parts and purified according to conventional techniques.

Natural inulin from chicory, respectively from J. artichoke, commonly appears as a polydisperse mixture of slightly branched chains (typically chains with less than 2 per cent, respectively less than 1 per cent, branching) with a (DP) ranging from 2 to about 70, respectively from 2 to about 40. Natural (standard grade) chicory inulin has a ($\overline{DP}$) of about 10 and natural (standard grade) inulin from J. artichoke has a ($\overline{DP}$) of about 6.

Natural inulin from agave appears as a polydisperse mixture of highly branched chains with a ($\overline{DP}$) commonly ranging from about 14 to about 17.

At industrial scale, chicory inulin is conventionally obtained by extraction of shredded chicory roots with hot water yielding a crude inulin solution which is subsequently purified by depuration (treatment with lime followed by carbonatation and filtration) and by refining (involving treatment over ion-exchangers, treatment with active carbon and filtration). Standard grade inulin is then commonly obtained from the purified and refined solution by spray-drying. Optionally, monomeric and dimeric saccharides are removed from the purified and refined solution (e.g. by column chromatographic separation as described in EP 0670 850) to yield via spray-drying an inulin grade with a standard ($\overline{DP}$) of about 10 which is about free of monomeric and dimeric saccharides. Optionally the purified and refined solution can be fractionated to remove monomeric and dimeric saccharides as well as oligofructose (e.g. by directed crystallisation as described in EP 0 769 026) and the fractionated inulin is then isolated in particulate form by spray-drying. Depending on the manufacturing process, chicory inulin with a ($\overline{DP}$) ranging from about 10 (standard grade) to about 30, and even more, can be obtained.

Similarly, agave inulin can be obtained at industrial scale by squeezing, or extracting with water, shredded heads or pulp from Blue Agave, followed by conventional purification, refining and isolation of the inulin e.g. via spray-drying.

Inulin, including linear and branched inulin, with a ($\overline{DP}$)≧20 is termed herein long-chain inulin, whereas linear and branched inulin with a ($\overline{DP}$) from 10 to <20 is termed herein medium-chain inulin.

Inulin from chicory is for example commercially available as RAFTILINE® from ORAFTI (Tienen, Belgium) in various grades. Typical grades are RAFTILINE® ST (with a ($\overline{DP}$) of about 10 and containing in total about 8% by weight glucose, fructose and sucrose) and RAFFILINE® HP (with a ($\overline{DP}$) of at least 20, commonly with a ($\overline{DP}$) of about 23 to about 25, and virtually free of glucose, fructose and sucrose).

Agave inulin is commercially available, for example industrial grade agave inulin as GAVEDIET® PR with a ($\overline{DP}$) of 14-16 and containing in total about 5% by weight of glucose and fructose, from Industrias Colibri Azul S.A. de C.V., Mexico.

Oligofructose can be obtained according to techniques which are known in the art, including enzymatic in vitro synthesis from sucrose, as for example described in U.S. Pat. No. 5,314,810, and partial hydrolysis of inulin, as for example described in EP 0 917 588.

Oligofructose prepared by enzymatic hydrolysis of chicory inulin is commercially available in various grades, for example as RAFTILOSE® from ORAFTI (Tienen, Belgium), e.g. RAFTILOSE® L95 (liquid form) or RAFTILOSE® P95 (powder form), both with a content of about 95% oligofructose (% is wt % on total carbohydrates) with a (DP) from 2 to 9, typically with a (DP) mainly from 2 to 7, a $(\overline{DP})$ of about 4.5, and containing about 5% in total (% is wt % on total carbohydrates) of glucose, fructose and sucrose, and RAFTILOSE® L85, liquid form with a content of about 85% oligofructose (% is wt % on total carbohydrates) with a (DP) from 2 to 9, typically a (DP) mainly from 2 to 7, a $(\overline{DP})$ of about 3.5, and containing about 15%, maximally 20% in total (% is wt % on total carbohydrates) of glucose, fructose and sucrose.

Unless otherwise specified, the term inulin used herein refers to linear as well as branched inulin, and includes inulin molecules with a (DP)<20 as well as inulin molecules with a (DP)≧20.

In the food and feed industry, oligofructose is widely used as a low-calorie partial or complete replacement for sugar, providing sweetness, body and mouthfeel, whereas inulin of a $(\overline{DP})$ of at least about 10, preferably of at least 20, is utilised (i) as a partial or complete low-calorie replacement for sugar in combination or not with one or more high intensity sweeteners, providing body and mouthfeel, (ii) as a texture improver, and (iii) as a low-calorie replacement for fat. The use of inulin as fat replacer results from the fact that inulin can form with water a particle gel with a stable, homogeneous, creamy structure with excellent organoleptic properties.

Inulin molecules with a (DP)≧10 as well as oligofructose molecules with a (DP)<10, are not hydrolysed by human digestive enzymes. Accordingly, these molecules pass the upper part of the digestive tract and the small intestine unaltered (Ellegård et al. (2)) and reach almost quantitatively the large intestine where they are fermented by specific intestinal bacteria (Roberfroid et al. (3)). As a result thereof, inulin and oligofructose present highly interesting nutritional properties.

Firstly, inulin and oligofructose are considered as dietary fibres. They reach the large intestine unaltered, thus providing carbon energy to the microflora in the large intestine. In this manner, inulin and oligofructose are stimulating the growth of gut bacteria in the large intestine which has a beneficial effect on the gut function, including a bulking effect (i.e. increase of the bacterial biomass) which in turn results in an increased stool weight, an increased stool frequency and a relief of constipation (Roberfroid (4)).

Furthermore, it has been found that inulin and oligofructose have a strong bifidogenic effect because inulin and oligofructose selectively stimulate the growth and metabolic activity of Bifidobacteria and Lactobacilli. Besides, while the counts of intestinal Bifidobacteria are significantly increased by the oral intake of inulin or oligofructose, a concomitant significant reduction of the counts of undesirable or pathogenic bacteria, such as e.g. Clostridia and Escherichia, in the large intestine has been observed (Gibson et al. (5) and Wang (6)). The intake of inulin and oligofructose thus largely modifies and modulates the gut flora by selectively increasing colonisation of the large intestine by beneficial bacterial species, typically Bifidobacteria, while suppressing the growth of undesirable bacterial species, which in turn results in favourable prophylactic and therapeutic effects on intestinal disorders of the host.

WO 93/02566 discloses a reduced calorie chocolate confectionery composition that is obtained by partial substitution of the sugar and/or fat of a conventional composition by a fructan or fructan mixture. WO 93/02566 furthermore discloses in a generic manner that a mixture of inulin and fructo-oligosaccharides presents good dietary fiber effects in combination with bifido-stimulating effects and good promotion of intestinal flora proliferation, but is silent about possibly improved nutritional and health effects that may result form mixtures of inulin and fructo-oligosaccharides that present a particular inulin profile.

WO 96/03888 relates to a water continuous edible spread that presents good structural properties (in particular plasticity) and no sweet off-taste. Several spread compositions respectively with low-sugar inulin of av. DP 12 (Raftiline® LS) and long-chain inulin (Fibruline® LC of av. DP 20 and oligofructose of av. DP 25) are described. The disclosed experimental data indicate that a water continuous spread with the desired properties is obtained when the spread composition comprises at least 7 wt % oligofructose having an av. DP of at least 14 whereby the short oligofructose molecules are present in very small amounts or not at all. WO 96/0388 is silent about possibly improved nutritional and health effects that may be provided by compositions of short-chain and long-chain inulin molecules presenting a particular inulin profile.

In vivo experiments with healthy volunteers showed inulin (RAFRILINE® ST) and oligofructose (RAFTILOSE® P95) to be bifidogenic to the same extent (Gibson et al. (7)), while in vitro experiments revealed that inulin ((DP)≧10) is fermented in the large intestine about twice as slowly as oligofructose ((DP)<10) (Roberfroid et al. (3)).

From these observations it follows that oligofructose is almost completely fermented in the proximal part of the large intestine, i.e. the ascendent part, whereas inulin is likely to reach to a more or lesser extent also more distal parts of the large intestine, i.e. the transversal and descendent parts, where it is fermented.

In vitro tests revealed that agave inulin is about as easily fermented as oligofructose. Accordingly, it is assumed that agave inulin is also almost completely fermented in the proximal part of the large intestine of humans and mammals.

Moreover, it has been disclosed that oligofructose and inulin have preventive and therapeutic effects with respect to the genesis and growth of certain cancers such as colon cancer (WO 98/52578) and mammary cancer (EP 0 692 252).

The effects against mammary cancer seem to be related to an immuno-modulating effect, particularly a stimulating effect on the immune system, of oligofructose, inulin and/or their fermentation products, mainly short chain fatty acids (SCFA) (Namioka et al. (8)).

With respect to colon cancer (usually resulting from pre-neoplastic lesion formation in the distal part of the colon), it has been reported that long-chain inulin, i.e. inulin with a ($\overline{DP}$)≧20, is more effective in preventing the genesis of colon cancer and in inhibiting the growth of colon cancer, than oligofructose (with a $(\overline{DP})$<10) and standard grade chicory inulin (with a $(\overline{DP})$ of about 10) (WO 98/52578).

Furthermore, it has been found in studies with healthy human volunteers who were slightly hyperlipidemic, that the consumption of oligofructose or inulin has beneficial effects on lipid metabolism since the consumption resulted in reducing the level of serum triglycerides and cholesterol (mainly LDL cholesterol) compared to a control placebo treatment (Brighenti et al. (9) and Jackson et al. (10)). Moreover, it has been demonstrated in rat experiments that the addition of oligofructose or inulin to a fat-rich diet reduced serum cholesterol as well as serum triglycerides by more than 50% compared to a control group (Kok et al. (11)).

Furthermore, positive effects of the consumption of oligofructose and inulin on the intestinal absorption of minerals, particularly calcium (Ca), magnesium (Mg) and iron (Fe), as well as on the bone mineral density (BMD), have been found in various studies. Shimura et al. (12), Levrat et al. (13), Rémésy et al. (14), Tagushi et al. (15) and Scholz-Ahrens et al. (16) reported studies with rats in which an increased absorption of calcium, and in some cases of other minerals, including magnesium, was demonstrated as a result of oral consumption of inulin or oligofructose. Ohta et al. (17) and Baba et al. (18) formulated the hypothesis that the positive effects of non-digestible carbohydrates on Ca and Mg absorption occur at the level of the large intestine. Up to then, it was generally accepted that mineral absorption occurred mainly via the small intestine. Delzenne et al. (19) reported that a diet supplemented with 10 wt % of either inulin (RAFTILINE®ST) or oligofructose (RAFTILOSE®P95) resulted in a strong absorption increase for magnesium and calcium and a moderate absorption increase for iron in healthy rats, and noted almost the same effect for inulin (RAFTILINE® ST) compared to oligofructose (RAFTILOSE® P95). Brommage et al. (20) disclosed a similar increase in Ca absorption in healthy rats fed a diet supplemented with 5 wt % oligofructose (RAFTILOSE® P95). Taguchi et al. (15) reported that in ovariectomised rats oligofructose (2.5 wt % and 5 wt % in the diet) increased mineral uptake, particularly Ca and Mg absorption, and increased bone density thus preventing bone loss caused by oestrogen deficiency. Using the same model, Scholz-Ahrens et al. (16) observed a dose-dependent effect of oligofructose (RAFTILOSE® P95) (at 2.5; 5 and 10 wt % in the diet) on calcium absorption and on bone mineralisation. In that study, oligofructose also significantly reduced the osteoporotic loss of the bone trabecular structure caused by ovariectomy. Furthermore, an increased Ca absorption with a concurring increased BMD in rats fed a diet containing 5 wt %, respectively 10 wt %, inulin (RAFTILINE® HP) was reported by Lemort et al. (21).

The findings that inulin and oligofructose can positively influence the absorption of minerals from the diet and affect the uptake of minerals in the bone tissue, leading to increased BMD, are of high importance for human health. Indeed, calcium uptake in the body, bone mineral density increase, as well as the possibility to prevent, to slow down or to curb bone mineral density reduction, are very important for human populations with a typical Western-type lifestyle and food pattern, since in these populations there occurs with increasing age, particularly in post-menopausal women, a dysbalance between mineral uptake and mineral resorption and excretion. Said dysbalance results in a reduction of BMD and in bone fragilisation, which in a pronounced stage is known as osteoporosis. In an advanced stage, osteoporosis leads in turn to a high incidence of bone fractures. Accordingly, it is very important to ensure the building up during the growth phase of children and adolescents of skeletal elements with a high BMD. Such skeletal elements will indeed resist longer to demineralisation caused by any factor, and this may thus postpone or even avoid bone fracture due to advanced osteoporosis. In view of the above, it is also most important to be able to reduce possible losses of bone mineral content in adults in order to prevent or to maximally delay undesirable osteoporosis-related conditions, and in particular to slow down the post-menopausal demineralisation leading to osteoporosis and eventually to bone fracture. Furthermore, it is very important to be able to remedy conditions of osteoporosis, in particular in case of the occurrence of osteoporosis-related bone fractures. At last, it is highly desirable to be able to stimulate and increase mineral uptake and formation of bone structure in case of necessity, for example in case of accidental bone fractures in children, adults and elderly people.

In view thereof, the disclosures regarding the increased mineral absorption in rats have received much attention from the medical world and several studies have been made in order to examine Ca absorption from the diet and to increase Ca uptake in the bone tissue, in order to increase or improve BMD and bone structure in humans. Ellegård et al. (2) determined the mineral balance in ileostomy volunteers who were administered 15 g/day of either inulin (RAFTILINE® ST) or oligofructose (RAFTILOSE® P95). The intake of neither inulin nor oligofructose was found to alter the mineral excretion from the small intestine, thus confirming that the effect of inulin and oligofructose on mineral absorption does not occur in the small intestine but essentially takes place in the large intestine (also termed the colon). Studies by Coudray et al. (22) with healthy male adults (metabolic balance method) showed a significantly increased Ca absorption with a dietary intake of 40 g inulin per day. In studies (dual stable isotopes method) with healthy male adolescents, Van den Heuvel et al. (23) found a significant increase in Ca uptake upon consumption of 15 g/day oligofructose (RAFTILOSE® P95).

The beneficially nutritional effects resulting from the intake of oligofructose and inulin apparently are the result of their fermentation in the large intestine. However, as reported by Roberfroid et al. (3), the fermentation rate of inulin is much slower than the one of oligofructose.

Furthermore, in vitro experiments (unpublished results) with human faecal slurries even indicated to the inventors that when long-chain inulin (i.e. inulin with $\overline{DP} \geq 20$), was essentially free from oligofructose, i.e. inulin of (DP)<10), its fermentation hardly started.

The above observations, on the one hand the improved nutritional effects of inulin, particularly of long-chain inulin, and, on the other hand, the difficult and slow start of the fermentation and the resulting low fermentation rate of inulin, particularly long-chain inulin, in the large intestine, clearly lead to a technical problem which limits and even prevents the use of long-chain inulin to maximally generate nutritional benefits in humans and mammals.

Furthermore, in most of the nutritional studies disclosed so far, a daily consumption of relatively high amounts of oligofructose or inulin have been used, namely 15 g to 40 g/day in human studies and 2.5 wt % to 10 wt % and even 20 wt % of the diet in rat studies. Extrapolated to humans, a rat diet containing 2.5 wt % to 10 wt % oligofructose or inulin would correspond to an amount oligofructose or inulin of about 15 g to 60 g/day. Such relatively high daily amounts also constitute a further technical problem for the use of inulin for nutritional purposes, particularly for generating improved beneficially nutritional effects in humans, because, as is known, such relatively high doses may cause intestinal side effects, such as too much flatulence, too much intestinal pressure, intestinal cramps and even diarrhoea.

Object of the Invention

It is an object of the present invention to provide a novel inulin product and compositions thereof presenting improved nutritional properties for humans, mammals and other vertebrates, compared to known inulin products, without imparting intestinal side effects.

It is another object of the present invention to provide a novel inulin product and compositions thereof which modulate the bacterial flora composition in the large intestine of humans, mammals and other vertebrates, and which modulate the fermentation pattern of inulin in said beings.

It is a further object of the present invention to provide the use of said novel inulin product and compositions thereof for the preparation of products and compositions for generating improved nutritional effects, in particular increased mineral absorption, in humans, mammals, and other vertebrates.

Description of the Invention

In the search for improved inulin products, the inventors have surprisingly found a novel inulin product comprising a hardly fermentable inulin such as e.g. a long-chain inulin that, in spite of the above adverse indications for using such an inulin, nevertheless provides a solution to one or more of the mentioned and other problems.

According to one embodiment of the present invention, the inulin product of the invention consists of a mixture of an easily fermentable inulin component (hereinafter EFI) and a hardly fermentable inulin component (hereinafter HFI) in a specific weight ratio EFI/HFI ranging from 10/90 to 70/30.

By easily fermentable inulin (EFI) is meant herein linear as well as branched inulin-type products which are completely or almost completely fermented in the proximal part (the ascendent part) of the large intestine of humans and mammals. Typical EFI are short-chain inulin (i.e. inulin with a (DP)<10) and agave inulin (i.e. a branched inulin, typically of $(\overline{DP})$ of 14 to 16).

Short-chain inulin has preferably a (DP) ranging mainly from 2 to 7, with minor amounts, in total preferably less than 5%, more preferably less than 3%, inulin of (DP)=8 and (DP)=9 (% is wt % on total inulin). A preferred short-chain inulin is oligofructose obtained by enzymatic hydrolysis of chicory inulin.

By hardly fermentable inulin (HFI) is meant herein linear as well as branched inulin-type products of which the fermentation hardly starts in the proximal part of the large intestine and which are mainly fermented, though at a low rate, in the distal part (the transversal part and/or the descendent part) of the large intestine of humans and mammals. Typical HFI are long-chain inulin (i.e. linear as well as branched inulin with a $(\overline{DP})\geqq 20$), and inulin in a particular crystallographic form or a particular physical appearance form which does not enable easy and significant fermentation in the proximal part of the large intestine of humans and mammals.

Long-chain inulin has preferably a $(\overline{DP})$ of at least 23, more preferably of at least 25, even more preferably of at least 30, and contains in total preferably less than 5%, more preferably less than 3%, inulin of (DP)=9 and (DP)=10 (% is wt % on total inulin).

A preferred HFI is long-chain inulin from chicory (named herein long-chain chicory inulin) with a $(\overline{DP})\geqq 20$, preferably a $(\overline{DP})\geqq 23$, more preferably a $(\overline{DP})\geqq 25$, and another preferred HFI is inulin from bacterial origin.

In a preferred embodiment, the inulin product of the invention consists of a mixture of a EFI component that is free from agave inulin and consists of a short-chain inulin, and a HFI component which is a long-chain inulin, in a weight ratio EFI/HFI ranging from 10/90 to 70/30, and wherein the total content of inulin with (DP)=9 and (DP)=10 is maximally 5%, preferably maximally 3%, more preferably maximally 2%, most preferably maximally 1% (% is wt % on total inulin, determined by gas liquid chromatography (GLC) analysis according to De Leenheer et al. (1)).

In an other preferred embodiment, the inulin product of the invention consists of a mixture of a EFI component consisting of agave inulin, preferably natural agave inulin with a $(\overline{DP})$ ranging from about 14 to about 17, or any mixture of agave inulin with a short-chain inulin, and a HFI component which is a long-chain inulin, in a weight ratio EFI/HFI ranging from 10/90 to 70/30, in which product the total amount of inulin with (DP)=9 and (DP)=10 is maximally 5%, preferably maximally 3%, more preferably maximally 2%, most preferably maximally 1% (% is wt % on total inulin, determined by GLC according to De Leenheer et al. (1)).

In a preferred inulin product according to the invention, said weight ratio of EFI/HFI is preferably ranging from 20/80 to 65/35, more preferably from 35/65 to 65/35, and even more preferably from 40/60 to 45/55, typically about 50/50.

In a more preferred embodiment, the inulin product of the invention consists of a mixture of oligofructose as EFI component and a long-chain chicory inulin as HFI component in an EFI/HFI weight ratio ranging from 10/90 to 70/30, wherein the total content of inulin with (DP)=9 and (DP)=10, is maximally 5%, preferably maximally 3%, more preferably maximally 2%, most preferably maximally 1% (% is wt % on total inulin, determined by GLC. In a highly preferred embodiment, the EFI/HFI weight ratio of the inulin product ranges from 35/65 to 65/35, most preferably from 40/60 to 45/55.

According to a further, highly preferred embodiment of the invention, the inulin product according to the invention is an industrial grade inulin product, which means an inulin product composed of a mixture of industrial grade short-chain inulin or agave inulin or any mixture thereof as EFI component and of industrial grade long-chain inulin as HFI component in a weight ratio EFI/HFI ranging from 10/90 to 70/30, preferably from 35/65 to 65/35, most preferably from 40/60 to 45/55, wherein the total content of inulin with (DP)=9 and (DP)=10 is maximally 5%, preferably maximally 3%, more preferably maximally 2% and most preferably maximally 1% (% is wt % on total inulin determined by GLC).

In the industrial grade inulin product according to the invention, the weight ratio EFI (short-chain inulin) component/HFI (long-chain inulin) component is defined on the basis of the real short-chain inulin and real long-chain inulin present in the respective components, without taking into account the amounts of glucose, fructose and sucrose which are possibly present. The real amount of inulin product of the invention in said industrial grade inulin product thus corresponds to the sum of the amounts of real short-chain inulin and real long-chain inulin present in the EFI and HFI components.

Accordingly, industrial grades of oligofructose can be used as EFI component in the industrial grade inulin product according to the invention, which may even contain in total maximally 20%, preferably maximally 15%, more preferably maximally 10%, even more preferably maximally 8%, most preferably maximally 5%, glucose, fructose and sucrose (%=wt % on total carbohydrates in the oligofructose product).

In still a further preferred industrial grade inulin product according to the invention, the oligofructose component consists of more than 43 wt % of inulin-type molecules of formula Fm wherein F indicates a fructosyl unit and m is the degree of polymerisation, ranging from 2 to 9, preferably mainly from 2 to 7.

Typically industrial grades of oligofructose which are suitable as EFI component of the industrial grade inulin product according to the invention are RAFTILOSE® L85, RAFTILOSE® L95 and RAFTILOSE® P95, which are all oligofructose grades obtained by enzymatic hydrolysis of chicory inulin. Suitable industrial grades of oligofructose can also be obtained by enzymatic in vitro synthesis from sucrose by known methods, for example according to patent U.S. Pat. No. 5,314,810. A suitable industrial grade of agave inulin is GAVEDIET®PR.

Industrial grade long-chain inulin with a $(\overline{DP}) \geqq 20$ which is suitable as HFI component of the industrial grade inulin product of the invention may contain inulin molecules with a (DP) from 10 to 20 up to about 45% (% is wt % on total carbohydrates). Possibly present inulin molecules with a (DP)<10 are calculated as part of the EFI component. In said industrial grade long-chain inulin, the content of glucose, fructose and sucrose is usually very low, typically less than about 2% (% is wt % on total carbohydrates).

A typically industrial grade inulin which is suitable as HFI component is long-chain chicory inulin with a $(\overline{DP}) \geqq 20$, preferably a $(\overline{DP}) \geqq 23$, such as RAFTILINE®HP.

The inulin product of the invention surprisingly presents significantly improved nutritional properties and its oral or enteral intake provides one or more significantly improved nutritional effects/benefits in humans, mammals and other vertebrates, compared to known inulin products, such as oligofructose, medium-chain inulin and long-chain inulin. Furthermore, the oral or enteral intake of the inulin product of the invention provides said improved nutritional effects/benefits in humans, mammals and other vertebrates, commonly at a lower daily dose than the daily dose which is needed of known inulin products to produce, if possible at all, such nutritional effects.

The mammals are particularly dogs, cats, horses, rabbits, pigs, piglets and calves.

The inulin product of the invention has the potential to quickly and significantly modify and modulate the composition of the bacterial flora in the large intestine, in the proximal part as well as in the distal part of the large intestine of humans, mammals and other vertebrates, which beings may be healthy, disfunctioned or diseased.

By disfunctioned humans, mammals and other vertebrates is meant herein non-diseased beings in which a bodily function is not functioning optimally, possibly leading to a higher risk for the development or leading to the development of a disease later on.

Without being bound by the following hypothesis, the inventors assume that the improved nutritional benefits of the inulin product of the invention result from the presence of an EFI component and a HFI component in the defined specific weight ratio, which is such that the specific amount of easily fermentable inulin in said inulin product selectively stimulates the growth and metabolic activity of Bifidobacteria and other beneficial bacteria in the proximal part of the large intestine of humans, mammals and other vertebrates, thus modifying and modulating the current bacterial flora into a flora composition much more consisting of beneficial bacteria and much less of undesirable bacteria than the current flora composition, and that these activated bacteria are dragged together with the specific amount of unaltered hardly fermentable inulin of the inulin product of the invention from said proximal part into the distal part of the large intestine. On arrival in the distal part, the activated bacteria, under pressure of the depletion of EFI (being consumed by the bacteria in the proximal part of the large intestine), trigger the fermentation of the HFI which, accordingly, will be quickly and completely fermented in the distal part (the transversal as well as the descendent part) of the large intestine. The inulin product of the invention thus provides on the one hand a HFI component which will reach almost unaltered the distal part of the large intestine where its fermentation is most beneficial, whereas on the other hand, through its EFI component, the inulin product of the invention ensures that the fermentation of said HFI in the distal part of the large intestine is readily started by activated bacteria and is proceeding well to complete fermentation, which in turn results in providing one or more improved inulin-associated nutritional effects/benefits. The inulin product of the invention thus has the potential to modify and/or modulate the fermentation pattern of inulin in the large intestine, particularly in the distal part of the large intestine of humans, mammals and other vertebrates.

In a further embodiment, the present invention relates to a method for preparing an inulin product according to the invention, consisting in mixing the EFI component and the HFI component in the above defined specific weight ratio. The mixing can be carried out by conventional techniques, such as for example by dry mixing of the components or by wet mixing of the components, optionally followed by isolation of the formed inulin product in dry form via conventional techniques, e.g. via spray-drying. Wet mixing techniques include (a) mixing of the components dissolved, dispersed or suspended in a liquid, optionally followed by isolation of the formed inulin product via known techniques such as e.g. spray-drying, (b) mixing one of the components in dry form (preferably in powder form), in neat form or in solution, dispersion or suspension in a liquid, into the other component in neat form, in solution, dispersion or suspension in a liquid, the liquids being preferably the same, optionally followed by isolation of the formed inulin product by known techniques, typically by spray-drying, (c) preparing separately a solution, dispersion or suspension of each of the components in a liquid, followed by mixing them and isolation of the formed inulin product of the invention through co-drying techniques, especially co-spray-drying, and (d) agglomerating a dry mixture of said components in powder form by moistening with water in the liquid or vapour phase, followed by drying of the moist mixture in the presence of hot air, typically in an agglomerating chamber, followed by cooling and isolation of the formed particles. The particles can then be sieved to isolate an inulin product of the invention with a desired particle size while the particles outside the desired size can be recycled.

The inulin product of the invention is preferably manufactured by co-drying, preferably co-spray-drying, of both components in the specific weight ratio or by spray-drying one component while bringing the pulverised jet of said component during the spray-drying step into contact with the second component in particle form, in the desired specific weight ratio, in the presence of hot air in a drying chamber, thus forming co-dried particles or agglomerates. Isolation of the formed particles or agglomerates can be made conventionally.

Optionally, the mixing process, typically the mixing process which involves a spray-drying step, can include a conventional UHT (ultra-high-temperature) treatment step in order to produce an inulin product of acceptable microbiological quality.

The liquids used in the preparation of the inulin product of the invention should preferably not provoke hydrolysis of the components to a significant extent since otherwise the required specific weight ratio of the components might not be fulfilled any longer. The most suitable liquid is water which is a good solvent for short-chain inulin and agave inulin, as well as for long-chain inulin (at least at a temperature above about 80° C.).

The process conditions of the wet mixing process should be appropriate which means that the combination of the process parameters, including kind of liquid, pH of the solution, dispersion or suspension, temperature, and retention time (i.e. the time the components and/or the formed inulin product remain in said conditions), are selected in such a manner that no, or at least no significant, hydrolysis or degradation of the components or of the formed inulin product occurs.

In a further embodiment the present invention relates to compositions containing an effective amount of the inulin product of the invention, and one or more edible or pharmaceutically acceptable components. Typical compositions include food, feed, drinks, functional food, functional feed, medicaments and pharmaceuticals (including prophylactic compositions and therapeutic compositions), and intermediates thereof.

By functional food or feed is meant food or feed containing a food or feed ingredient that may provide a health benefit beyond the traditional nutrients it contains (definition according to the Institute of Medicine of the National Academy of Sciences (USA; 1994).

Said edible or pharmaceutically acceptable components are preferably selected from the group consisting of sugars (for example: glucose, fructose, sucrose, lactose, galactose, maltose, isomaltulose), polyols (for example: sorbitol, lactitol, maltitol, isomalt, mannitol, xylitol), maltodextrins, sweeteners, hydrogenated glucose syrups, food or feed additives, food or feed ingredients, food or feed intermediates, food or feed products, liquids, drinks, sources of minerals, particularly sources of calcium, of magnesium and of iron, pharmaceutically acceptable excipients, therapeutically active substances, medicaments and pharmaceutical compositions containing one or more active ingredients.

By effective amount is meant herein an amount of the inulin product of the invention which provides said improved nutritional effects/benefits in humans, mammals and other vertebrates when the composition is orally or enterally taken, preferably regularly taken at a daily dose.

A particularly advantageous and preferred composition according to the present invention comprises the inulin product of the invention in the presence of an edible or pharmaceutically acceptable, bio-available source of one or more minerals, particularly a source of calcium and/or magnesium and/or iron, such as for example dairy products and salts and complexes of calcium, magnesium and iron.

Typically the bio-available amount of a mineral in said source of minerals that is present in a daily dose of the composition of the invention equals an amount which corresponds to the recommended daily dose (RDI value) for said mineral. However, said composition may also contain less or more of said bio-available mineral than the recommended daily dose.

The compositions according to the invention can be prepared by conventional techniques, including, for example, mixing an inulin product of the invention with at least one edible or pharmaceutically acceptable component, or, alternatively, by mixing the EFI component and the HFI component in the specified weight ratio according to the invention, together with one or more of said edible or pharmaceutically acceptable components, optionally followed by bringing the obtained composition in a desired form by conventional techniques. The composition of the invention may appear as a solid, a semi-solid such as a cream or paste, a gel, a liquid, a dispersion, a suspension or an emulsion, in any desired form.

The composition may appear, for example, in the form of all kinds of food, feed, drink, functional food and functional feed, e.g. as bread, cookies and biscuits, cheese and other dairy products, chocolate, jam, pudding and other dairy desserts, spreadable products, frozen desserts and ice-cream; in the form of a pharmaceutical composition and medicament, e.g. as a powder, an aggregate, a granulate, a tablet, a coated tablet, a lozenge, a capsule, a drink, a syrup, a composition for tube feeding, for enteral intake, for oral administration and for enteral administration.

Furthermore, the inulin product of the invention and composition thereof can be in the form of a consumer product, being a product or composition presented in the form and/or package which allows its direct use by the consumer, for example in the form of tablets, granules or powder preferably packed in a unit dose.

In a further aspect, the present invention relates to the use of an inulin product or a composition according to the present invention as a food, a feed, a drink, a consumer product, a functional food, a functional feed, a pharmaceutical, a medicament, or an intermediate thereof.

In a further aspect, the present invention relates to the use of an inulin product or a composition according to the present invention, by oral and/or enteral intake or administration, preferably of a daily dose, for modifying and modulating the bacterial flora composition in the large intestine, particularly in the distal part of the large intestine, and/or for modifying and modulating the fermentation pattern of inulin, in healthy, disfuntioned or diseased humans, mammals and other vertebrates, as well as for providing one or more improved inulin-associated nutritional effects/benefits in humans, mammals and other vertebrates, which beings may be healthy, disfuntioned or diseased.

In a further embodiment, the present invention relates to the inulin product and a composition according to the invention, for use as a food, feed, drink, consumer product, composition, functional food, functional feed, pharmaceutical, medicament, or intermediate thereof, in particular for modifying and modulating the bacterial flora composition in the large intestine, particularly in the distal part of the large intestine, for modifying and modulating the fermentation pattern of inulin, as well as for providing one or more improved inulin-associated nutritional effects/benefits, in humans, mammals and other vertebrates, which beings may be healthy, disfuntioned or diseased.

In still a further embodiment, the present invention relates to the use of an inulin product and a composition according to the invention for the manufacture of a composition, food, feed, drink, consumer product, functional food, functional feed, pharmaceutical, medicament, or intermediate thereof, particularly for modifying and modulating the bacterial flora composition in the large intestine, particularly in the distal part of the large intestine, for modifying and modulating the fermentation pattern of inulin, as well as for providing one or more improved inulin-associated nutritional effects/benefits in healthy, disfuntioned or diseased humans, mammals and other vertebrates.

Said improved inulin-associated nutritional effects/benefits include dietary fibre effects, particularly in the colon, more particularly in the distal part of the colon, including the generation of beneficial metabolites such as short chain fatty acids (SCFA's) and the generation of bacterial biomass, the reduction of the colonic pH, a prebiotic action and/or a bifidogenic effect, particularly in the distal part of the large intestine, including an increase of the counts of Bifidobacteria with a concurrent reduction of the counts of non-desirable and/or pathogenic bacteria, which in turn will benefit the prevention and treatment of intestinal disfunctions, disorders and diseases.

Furthermore, said improved nutritional effects/benefits also include a modulation of the lipid metabolism, a stimulation of the immune system, the reduction of the risk of cancer, and preventive and therapeutic effects against cancer, particularly against mammary cancer and colon cancer.

Further effects/benefits include improved absorption of minerals in the body, particularly of calcium and magnesium, improvement of the bone mineral density and of the bone structure in healthy, disfunctioned or diseased humans, mammals and other vertebrates, and the possibility to prevent, delay, curb or significantly reduce the bone demineralisation process and osteoporosis in humans, particularly in post-menopausal women, in gastrectomised humans, in elderly persons and in diseased humans, particularly in humans suffering from osteoporosis.

Moreover, said effects/benefits also enable the building up of a strong skeleton in growing children, growing adolescents, in growing mammals and other vertebrates, and to increase in humans the peak bone mass, which in turn enables to prevent or postpone bone demineralisation and osteoporosis later in life, particularly in post-menopausal women.

Furthermore, the inventors surprisingly found that the amount of EFI present in the inulin products of the invention exerts such a pronounced activating effect on the intestinal flora that the amount of HFI present in said products is readily and completely fermented in the distal part of the large intestine. This property of said inulin products of the invention results in the fact that the improved nutritional effects/benefits can be obtained by a lower daily dose of said inulin products compared to the daily dose of known inulin products which is required to obtain a similar effect, if possible at all. The said improved nutritional effects/benefits in humans, e.g. improved mineral absorption, are indeed already obtained with a daily dose in adults of as little as about 4 g inulin product of the invention, either as the inulin product per se (included also the industrial grade inulin product) or in a composition (g is gram of the real inulin product according to the invention).

The daily dose of real inulin product of the invention suitable for generating said improved nutritional effects/benefits in adults preferably ranges from about 4 g to about 12 g, corresponding to about 50 mg to about 150 mg/day/kg body weight, more preferably from about 6 g to about 10 g, and is typically about 8 g, and for babies and children the daily dose preferably ranges from about 40 mg to about 400 mg/day/kg body weight. Said small daily dose of inulin product of the invention results in considerable additional benefits for humans since it increases the comfort of the inulin intake compared to the rather large corresponding quantities of known inulin products (ranging from about 15 g to about 40 g per day) that are required for generating similar effects/benefits, if possibly at all. Besides, as a result of said small daily taken quantity of inulin, the humans will not encounter the intestinal side effects which are often associated with the intake of rather large quantities of inulin, such as flatulence, intestinal pressure, bloating, intestinal spasms and/or diarhoea.

Although the particular improved nutritional effects/benefits of the inulin product of the present invention have been explicitly disclosed herein with respect to humans and mammals, it has to be noted that the oral and/or enteral intake of the inulin product of the present invention also generates one or more of said improved nutritional effects/benefits, in other vertebrates, in spite of the possibly different digestive system of the latter animals compared to the systems of humans and mammals. The said vertebrates include fish, for example: salmon and turbot; amphibians; reptiles; and birds, for example: ostriches and poultry, particularly chicken and turkey.

DETAILED DESCRIPTION OF THE FIGURES

FIG. 1: represents a dionex chromatogram of an inulin product according to the invention consisting of a mixture of EFI (oligofructose with a (DP) mainly from 2 to 7 ) and HFI (chicory inulin with a (DP) of about 25 ) in a weight ratio 45/55.

The invention is further illustrated by the examples below:

EXAMPLE 1

Rat Study to Evaluate the Effect of the Intake of an Inulin Product According to the Invention Compared to Oligofructose and Long-chain Inulin on the Absorption of Calcium Calcium absorption was measured in four groups of Wistar male rats (groups of 9 or 10 rats; age of 6 weeks; weight of 160-180 g):

group 1: control group, receiving a diet of standard semi-synthetic food corresponding to the recommendations of the American Institute of Nutrition with mineral content according to AIN 1976;

group 2: group receiving said standard semi-synthetic food containing industrial grade oligofructose of (DP) mainly from 2 to 7;

group 3: group receiving said standard semi-synthetic food containing industrial grade long-chain chicory inulin with a ($\overline{DP}$) of about 25;

group 4: group receiving said standard semi-synthetic food containing an inulin product according to the invention consisting of industrial grade oligofructose of (DP) mainly from 2 to 7 and industrial grade long-chain chicory inulin with a ($\overline{DP}$) of about 25, in a weight ratio real EFI/real HFI of 45/55, prepared by co-spray-drying, corresponding to the product of FIG. 1.

After gradual adaptation of the rats to the diet during three weeks, the rats were kept for a fourth week in metabolic cages and received the respective diet containing 10 wt % of the tested oligofructose or inulin product (100 g food+100 g water per day). Food intake was monitored and the last four days of the fourth week the faeces and urine were collected to determine the digestive absorption of calcium. Calcium in urine samples was determined by atomic absorption spectrometry. Samples of the diet and of the lyophilised and grounded faeces were calcinated at 500° C., and the ashes were taken up in nitric acid/hydrogen peroxide, and after dilution with milli-Q water, calcium was determined by atomic absorption spectrometry.

The digestive absorption was calculated by the following formula:

daily digestive absorption = quantity orally taken − quantity excreted via the faeces;

% digestive absorption = 100 ×

{(quantity orally taken − quantity excreted via the faeces)/quantity orally taken}

The results are presented in Table 1 below.

The data of Table 1 show that compared to the control group, and taking into account that the urinary excretion of calcium did not differ amongst all 4 groups, calcium absorption was increased in all test groups, but only the increase of calcium absorption in group 4 (by about 20%) was found to be statistically significant versus the control group.

TABLE 1

Effect of oral intake of oligofructose or inulin on the intestinal absorption of calcium in the rat.

| | Digestive calcium absorption (%) | | | |
|---|---|---|---|---|
| | Group 1** (control) | Group 2** (oligofructose) | Group 3** (long-chain inulin) | Group 4 (inulin product of invention) |
| M ± SD* | 47.9 ± 5.5 | 52.7 ± 6.0 | 54.1 ± 5.6 | 58.1 ± 7.4 |
| min-max | 39.1-55.9 | 44.0-63.1 | 45.0-61.3 | 50.1-61.2 |

*Mean value ± standard deviation;
**comparative

EXAMPLE 2

Human Study to Evaluate the Effect of the Intake of an Inulin Product According to the Invention Compared to Oligofructose on the Calcium Absorption in Young Adolescent Girls Calcium absorption was measured in adolescent, healthy girls (11 to 14 years old; of 44 kg mean body weight). Ethical approval and informed consent were obtained in all cases. Only subjects were elected for the study with habitual calcium intakes between 500 mg and 1400 mg/day. Subjects were excluded from the study if they had a chronic gastrointestinal disease, renal failure, or disorders of calcium homeostasis, if they were taking prescription medication, smoking, were on a contraceptive pill or had a weight greater than the $90^{th}$ percentile for age. The subjects were studied using a randomised, double-blind, cross-over design. The subjects were randomised in two separate groups to receive two packets of 4 g servings of oligofructose or inulin product according to the invention daily for 3 weeks and two packets of 4 g servings of placebo daily for 3 weeks. The studies were separated by a 2-week wash-over period. The subjects received oligofructose or inulin product of the invention and placebo in a random order, and the investigators were blinded to the treatment assignment.

Two identical protocols were carried out simultaneously. In Protocol I (n=30) the test product was industrial grade oligofructose with (DP) mainly from 2 to 7. In Protocol II (n=29) the test product was an inulin product according to the invention, composed of a mixture of industrial grade oligofructose with (DP) mainly from 2 to 7 and industrial grade long-chain chicory inulin with a ($\overline{DP}$) of about 25, in a weight ratio of 45/55 (weight ratio on total real short-chain inulin and real long-chain inulin content), prepared by co-spray-drying, corresponding to the product of FIG. 1. In both protocols the placebo was packed and presented in an identical manner to the oligofructose/inulin. At the end of each 3-week adaptation period (to 8 g/day), calcium absorption was measured using a previously validated dual tracer stable isotopes technique. Furthermore, a baseline urine sample was collected from the subjects. The subjects consumed a low-calcium breakfast and a glass of calcium fortified orange juice to which was added one 4 g packet of oligofructose, inulin product or placebo, and 10 mcg of $^{46}$calcium. Immediately after breakfast 1.5 mg of $^{42}$calcium was infused intravenously over 2 to 3 minutes. The mid-day meal contained approximately 400 mg calcium either as calcium fortified orange juice, milk or yoghurt. The evening meal contained another serving of calcium fortified orange juice, 10 mcg of $^{46}$calcium and another 4 g packet of oligofructose, inulin product or placebo. The subjects consumed daily approximately 1300 mg calcium during the 8 week-study. A 48 hour urine collection was started immediately after isotope administration. Calcium absorption was measured by the ratio of the cumulative fractional excretion of the oral and intravenous isotopes in the 48 hour urine collection. Samples were purified using an oxalate precipitation method and isotope ratios were measured by thermal ionization magnetic sector mass spectrometry.

Compliance was assessed by a count of opened and unopened packets and any packet not accounted for was assumed to be unopened. The compliance for oligofructose and for the inulin product of the invention was very good as is shown by the data presented in Table 2 below.

TABLE 2

| Compliance | | |
|---|---|---|
| compliance | oligofructose** | inulin product of invention |
| Mean ± SD* | 95% ± 7 | 94% ± 12 |

*Mean value ± standard deviation;
**comparative

The results of the calcium measurements are given in Table 3 below.

TABLE 3

| Calcium absorption in healthy adolescent girls | | |
|---|---|---|
| Protocol carbohydrate | Calcium absorption % (as Mean ± SD)* | p-value versus placebo (sucrose) |
| Protocol I | | |
| sucrose** | 30.9 ± 10.0 | |
| oligofructose** | 31.8 ± 9.3 | 0.75 |
| Protocol II | | |
| sucrose** | 32.3 ± 9.8 | |
| inulin product of the invention | 38.2 ± 9.8 | 0.007 |

*Mean value ± standard deviation;
**comparative

The results in Table 3 indicate that there was no significant difference (p=0.89) in calcium absorption between Protocol I and Protocol II with sucrose (placebo), and also that oligofructose did not significantly alter calcium absorption. With the inulin product according to the invention, however, a significant increase in calcium absorption was obtained versus the placebo and also vis à vis oligofructose, i.e. from 31.8% to 38.2%, which corresponds to a relative increase of calcium absorption of 20%.

Moreover, the study of the urinary calcium excretion showed that, as seen from the data presented in Table 4 below, there were no significant differences in urinary calcium excretion between any of the study groups.

From the above experiment it can be concluded that, at the currently recommended intake of calcium (about 1300 mg/day for adolescent girls), the intake of an amount as little as 8 g/day inulin product according to the invention significantly increased the calcium absorption, without a compensatory increase in urinary calcium excretion, whereas the intake of 8 g/day oligofructose by the same population under the same experimental conditions did not significantly increase calcium absorption.

TABLE 4

Urinary calcium excretion in healthy adolescent girls

| Protocol carbohydrate | Urinary calcium excretion mg/day (M ± SD)* | p-value versus placebo (sucrose) |
|---|---|---|
| Protocol I | | |
| sucrose** | 71 ± 48 | |
| oligofructose** | 79 ± 50 | 0.75 |
| Protocol II | | |
| sucrose** | 65 ± 54 | |
| inulin product of the invention | 71 ± 50 | 0.57 |

*Mean value ± standard deviation;
**comparative

EXAMPLE 3

Rat Study Evaluating the Effect of the Intake of an Inulin Product of the Invention Compared to Oligofructose on the Absorption of Magnesium Magnesium absorption was measured in Wistar male rats (groups of 9 or 10 rats; age of 6 weeks; weight of 160-180 g) with:
- group 1: control group, receiving a diet of standard semi-synthetic food corresponding to the recommendations of the American Institute of Nutrition with mineral content according to AIN 1976;
- group 2: group receiving said standard semi-synthetic food containing industrial grade oligofructose of (DP) mainly from 2 to 7;
- group 3: group receiving said standard semi-synthetic food containing an inulin product according to the invention consisting of industrial grade oligofructose of (DP) mainly from 2 to 7 and industrial grade long-chain chicory inulin with a ($\overline{DP}$) of about 25, in a weight ratio real short-chain inulin/real long-chain inulin of 45/55, prepared by co-spray-drying, corresponding to the product of FIG. 1.

After three weeks of gradual adaptation to the diet, the rats were kept for a fourth week in metabolic cages and received their respective diet which contained 10 wt % of the tested oligofructose or inulin product (100 g food+100 g water per day). Food intake was monitored and the last four days of the fourth week the faeces and urine were collected to determine the digestive absorption of magnesium. Magnesium was determined in the samples of urine, faeces and feed, by atomic absorption spectrometry and the digestive magnesium absorption was calculated as indicated in Example 1.

The results are shown below in Table 5.

TABLE 5

Effect of oral intake of oligofructose or inulin product on the intestinal absorption of magnesium in the rat.

| | Digestive magnesium absorption (%) | | |
|---|---|---|---|
| | Group 1** (control) | Group 2** (oligofructose) | Group 3 (inulin product of invention) |
| Mean ± SD* | 48.8 ± 5.3 | 71.3 ± 4.5 | 76.7 ± 6.7 |
| min-max | 39.3-57.0 | 65.0-78.6 | 67.6-90.4 |

*Mean value ± standard deviation;
**comparative

The data of Table 5 show that, compared to the control group, magnesium absorption was statistically significantly increased in groups 2 and 3, in particular in group 3 with a relative increase of magnesium absorption of about 57%, and that the increase in magnesium absorption was more pronounced with the inulin product of the invention than with oligofructose.

EXAMPLE 4

Evaluation of the Effect of the Intake of an Inulin Product of the Invention Compared to Oligofructose and Long-chain Inulin on Lipid Metabolism in the Rat The effect of oligofructose and inulin products on lipid metabolism was measured in Zucker male rats. Zucker rats have a mutation of the leptine receptor which makes that these rats rapidly develop fat tissue instead of lean meat tissue and present as further characteristics hypertriglyceridemia, insulin resistance and hepatic steatose.

The following groups of rats (groups of 7 rats; age of 5 weeks) were involved in the study:
- group 1: control group, receiving a diet of standard feed;
- group 2: group receiving a diet of said standard feed containing oligofructose of (DP) mainly from 2 to 7;
- group 3: group receiving a diet of said standard feed containing long-chain chicory inulin with a ($\overline{DP}$) of about 25;
- group 4: group receiving a diet of said standard feed containing an inulin product according to the invention consisting of oligofructose of (DP) mainly from 2 to 7 and long-chain chicory inulin with a ($\overline{DP}$) of about 25, in a weight ratio real short-chain inulin/real long-chain inulin of 45/55.

After one week of adaptation to the diet (control diet or diet containing respectively 5 wt % of oligofructose, long-chain inulin or inulin product according to the invention), the rats received the study diet containing 10 wt % of the respective tested product for 6 weeks and were then sacrificed. Then, according to standard techniques, the parameters fat tissue weight, liver weight, concentration of liver triglycerides and activity of the enzyme fatty acid synthase in the liver were determined.

The results are presented in Table 6 below.

TABLE 6

Effect of oligofructose or inulin products on biometric and biochemical parameters in Zucker rats

| Group | Fat tissue weight (g) * | Liver weight (g) * | Liver triglycerides (mg/g liver) * | Activity of liver fatty acid synthase (FAS (mU/mg protein) * |
|---|---|---|---|---|
| 1 (control)** | 5.94 ± 0.23 | 18.32 ± 0.40 | 452.44 ± 72.05 | 32.31 ± 1.88 |
| 2 (oligofructose)** | 5.70 ± 0.23 | 17.28 ± 0.67 | 414.97 ± 50.12 | 22.4 ± 2.6 |
| 3 (long-chain inulin)** | 6.06 ± 0.28 | 18.17 ± 1.32 | 500.66 ± 62.68 | 25.3 ± 2.6 |
| 4 (inulin product of invention) | 4.99 ± 0.19 | 14.83 ± 0.60 | 286.64 ± 47.73 | 13.7 ± 0.52 |

* Mean value ± standard deviation;
**comparative

From the data of Table 6 it clearly follows that the inulin product according to the invention has the most pronounced effect on lipid metabolism compared to oligofructose and long-chain inulin.

EXAMPLE 5

Evaluation of the Effect of an Inulin Product of the Invention on Azoxymethane (AOM) Induced Carcinogenesis in Rat Colon Carcinogenesis is known to be a complex multi-step process that commonly occurs in three stages, named initiation, promotion and progression. Initiation is defined as exposure of normal cells to carcinogenic agents, such as certain chemicals, resulting in changes of the genomic level which promote selective growth of the cells. Promotion involves clonal expression of the initiated cells that is generally associated with altered morphological and/or phenotypic changes. Progression involves genotypic and phenotypic changes, associated with malignancy and metastasis.

Aberrant crypt foci (ACF) are putative precursor lesions from which adenomas and carcinomas may develop in the colon. Inhibitors of ACF formation have been shown to reduce the incidence of colon tumours in laboratory animals (Wargovich et al., (24)). Based upon these findings, ACF induction in animal models can be used to evaluate compounds for their potential preventive and therapeutic properties against colon cancer.

Example 5 describes an experiment wherein the effect of an inulin product of the invention on AOM induced ACF formation in rat colon has been evaluated in comparison with known inulin products. The experiment was run as follows.

The animals involved were male Fisher 344 weanling rats that were, after one week of acclimatisation on control diet, divided into the desired number of groups and assigned control food based on AIN93G diet or experimental food being control food but containing the evaluated product (10 wt %) at the expense of corn starch. Feed and water were provided ad libitum. Weekly body weights and daily feed intakes were recorded. After two weeks on the assigned diet, all animals received a subcutaneous injection of AOM (Sigma, St. Louis Mo., USA) in saline at 16 mg/kg body weight at 7 and 8 weeks of age. At the end of the feeding period which was eight weeks after the last AOM injection, the animals were sacrificed using $CO_2$ euthanasia. The colons were removed, flushed with potassium phosphate buffer and then fixed overnight with 10% buffered formalin. The colons were cut into proximal and distal portions of equal length, which in turn were cut into 2 cm long segments. The segments were examined, after staining with 0.5% methylene blue, under a light microscope, for ACF or tumours, and the total number of ACF as well as the number of crypts per focus were scored.

The data were analysed using the SAS statistical program and means were separated using the Tukey's Studentized Range Test.

The composition (in g/kg) of the diets is shown in Table 7.

TABLE 7

Composition of the diets used in the experiment

| | control diet** amended to contain (g/kg) | | |
|---|---|---|---|
| Animal group | corn starch | inulin product# | type of inulin product# |
| Group 1* (Control group) | 397.5 (=control diet) | 0.0 | — |
| Group 2* | 297.5 | 100.0 | RAFTILINE ® HP |
| Group 3* | 297.5 | 100.0 | RAFTILINE ® ST |
| Group 4* | 297.5 | 100.0 | RAFTILOSE ® P95 |
| Group 5 | 297.5 | 100.0 | Inulin product of invention |

*comparative test
**Control diet (in g/kg): corn starch (397.5); inulin product (0.0); casein (85% protein) (200); dextrinized corn starch (90-94% tetracharides) (132); sucrose (100); soybean oil (no additive) (70); Fiber (Solka-Floc ®, 200FCC of FS&D, St. Louis, MO, USA or equivalent) (50); mineral mix (AIN 93G-MX) (35); vitamin mix (AIN-93 VX) (10); L-cystine (3); choline bitartrate ((41.1% choline) (2.5).
products obtained from ORAFTI ® (Belgium): RAFTILINE ® HP (long-chain chicory inulin with a (DP) of about 25); RAFTILINE ® ST (standard grade chicory inulin with (DP) of about 12); RAFTILOSE ® P95 (industrial grade oligofructose of (DP) mainly from 2 to 7); Inulin product of invention: consisting of industrial grade oligofructose of (DP) mainly from 2 to 7 and industrial grade long-chain chicory inulin with a (DP) of about 25, in a weight ratio real short-chain inulin/real long-chain inulin of 45/55, prepared by co-spray-drying, corresponding to the product of FIG. 1.

Results:

No statistically significant difference was found in body weight gains and in mean daily feed intake between rats fed control diet and experimental diets. A small group of rats (blanco control group) receiving no AOM but only saline and fed the control diet showed no evidence of ACF formation in the colon. Results concerning the induction by AOM of ACF in rat colon are shown in Table 8 below.

TABLE 8

Effect of inulin products on ACF induction in rat colon by AOM

| Group | number of animals | ACF in proximal part | ACF in distal part | ACF total |
|---|---|---|---|---|
| Group 1* (Control) | 12 | 39.92 ± 0.82$^a$ | 114.17 ± 1.57$^a$ | 155.42 ± 1.64$^a$ |
| Group 2* (RAFTILINE ® HP) | 10 | 13.30 ± 1.45$^c$ | 70.20 ± 1.18$^c$ | 83.50 ± 1.67$^c$ |

TABLE 8-continued

Effect of inulin products on ACF induction in rat colon by AOM

| Group | number of animals | ACF in proximal part | ACF in distal part | ACF total |
|---|---|---|---|---|
| Group 3* (RAFTI- LINE ® ST) | 10 | 14.20 ± 0.57$^c$ | 93.90 ± 1.75$^b$ | 109.50 ± 2.15$^b$ |
| Group 4* (RAFTI- LOSE ® P95) | 10 | 24.80 ± 1.32$^b$ | 92.10 ± 1.35$^b$ | 116.90 ± 1.24$^b$ |
| Group 5 (Inulin product of invention) | 12 | 14.90 ± 0.94$^c$ | 63.00 ± 2.05$^d$ | 75.90 ± 1.54$^d$ |

$^{abcd}$Means ± SEM within the column with different letters are significantly different (p < 0.05) by Tukey's Studentized Range Test.
*comparative test From Table 8 it follows that by AOM treatment ACF were induced in the proximal as well as in the distal part of the rat colon, but predominantly in the distal part.

From Table 8 it further follows that ACF induction by AOM in the proximal part as well as in the distal part of the rat colon is reduced by various inulin products, including RAFTILINE® HP, RAFTILINE® ST, RAFTILOSE®P95, but significantly better by the inulin product according to the invention, as also shown in Table 9 below in which said reduction is presented in percent compared to the control group.

TABLE 9

Reduction in ACF induction in rat colon by diets containing inulin products

| | Reduction by diets containing inulin products of ACF induction in rat colon by AOM (% compared to control group) | | |
|---|---|---|---|
| Group | proximal part | distal part | total |
| Group 1* (Control group) | — | — | — |
| Group 2* (RAFTILINE ® HP) | 66.7 | 38.5 | 46.3 |
| Group 3* (RAFTILINE ® ST) | 64.4 | 17.8 | 29.5 |
| Group 4* (RAFTILOSE ® P95) | 37.9 | 19.3 | 24.8 |
| Group 5 (Inulin product of invention) | 62.7 | 44.8 | 51.2 |

*comparative test

From these results it clearly follows that the inulin product according to the invention inhibits in a much stronger manner than short-chain inulin, standard grade chicory inulin, and long-chain chicory inulin the induction of AOM induced ACF in rat colon.

Accordingly, the inulin products of the present invention are considered to be much more effective in the prevention and reduction of the risk of developing cancer as well as in the treatment of cancer, particularly colon cancer, in humans, mammals and other vertebrates, than short-chain inulin, standard grade inulin and long-chain inulin.

References (1) De Leenheer L. et al., Starch/Stärke, 46, (5), 193-196, (1994) and Carbohydrates as Organic Raw Materials, Ed. H. Van Bekkum et al. for CRF, Wageningen, TheNetherlands, Vol. III, 67-74, (1996)
(2) Ellegård L. et al., Eur. J. Clin. Nutr., 51, 1-5, (1997)
(3) Roberfroid M. et al., J. Nutr., 128 (1), 11-19, (1998)
(4) Roberfroid M., in Dietary Fiber in Health and Disease, (Ed. Kritchevsky, Bonfield), Plenum Press, New York, 211-219, (1998)
(5) Gibson G. R. et al., J. Appl. Bacteriology, 77, 412-420, (1994)
(6) Wang X., Ph. D. Thesis, University of Cambridge, UK, (1993)
(7) Gibson G. R. et al., Gastroenterology, 108, 975-982, (1995)
(8) Namioka S. et al., Bifidobacteria microflora, 10, 1-9, (1991)
(9) Brighenti F. et al., Eur. J. Clin. Nutr., 53(9), 726-733, (1999)
(10) Jackson K. G. et al, Brit. J. Nutr., 82 (1), 23-30, (1999)
(11) Kok N. et al., J. Nutr., 128 (7), 1099-1103, (1997)
(12) Shimura S. et al., J. Nutr. Food Sci., 44 (4), 287-291, (1991)
(13) Levrat M. A. et al., J. Nutr., 121, 1730-1737, (1990)
(14) Rémésy C. et al., Am. J. Physiology, 264 (5), G855-G862, (1993)
(15) Taguchi A. et al., Meiji Seika Kenkyu Nenpo, 33, 37-43, (1995)
(16) Scholz-Ahrens K. et al., Symposium Deutsche Gesellschaft für Ernahrungsforschung, 19-20 March 1998 (Kiel, Germany)
(17) Otha A. et al., J. Nutr., 125 (9), 2417-2424, (1995)
(18) Baba S. et al., Nutr. Res., 16 (4), 657-666, (1996)
(19) Delzenne N. et al., Life Science, 57 (17), 1579-1587, (1995)
(20) Brommage R. et al., J. Nutr., 123 (12), 2186-2194, (1993)
(21) Lemort C. et al., Thesis, Univ. Cathol. Louvain (1998)
(22) Coudray C. et al., Eur. J. Clin. Nutr., 51 (6), 375-380, (1997)
(23) Van den Heuvel E. et al., Am. J. Clin. Nutr., 69, 544-548, (1999)
(24) Wargovich M. et al., Cancer Epidemiol., Biomarkers, Prev., 5 (5), 355-360, (1996)

The invention claimed is:

1. An inulin product comprising a mixture of an easily fermentable inulin (EFI) component and a hardly fermentable inulin (HFI) component, wherein the weight ratio EFI/HFI ranges from 10/90 to 70/30, the EFI component comprises agave inulin or a mixture of agave inulin with a short-chain inulin with a (DP) <10, the HFI component comprises a long-chain inulin with a (DP)≧20, and the total amount of inulin with (DP)=9 and (DP)=10 is maximally 5% (% is wt % on total inulin, determined by GLC).

2. The inulin product according to claim 1, wherein the total content of inulin with (DP)=9 and (DP)=10 is maximally 2%.

3. The inulin product according to claim 1, wherein the total content of inulin with (DP)=9 and (DP)=10 is maximally 1%.

4. The inulin product according to claim 1, wherein the weight ratio of the EFI/HFI components ranges from 35/65 to 65/35.

5. The inulin product according to claim 1, wherein the HFI component consists of long-chain chicory inulin.

6. The inulin product according to claim 1, wherein the EFI component comprises a mixture of industrial grade oligofructose containing maximally 20% in total of glucose, fructose and sucrose (% is wt % on total carbohydrates) or industrial grade agave inulin, or a mixture of said oligofructose and said agave inulin as EFI component, and the HFI component comprises an industrial grade long-chain inulin.

7. The inulin product according to claim 6, wherein the HFI component comprises industrial grade long-chain chicory inulin.

8. The inulin product according to claim 6, wherein the short-chain inulin comprises industrial grade oligofructose containing maximally 8% in total of glucose, fructose and sucrose (% being wt % on total carbohydrates).

9. Method for preparing an inulin product according to claim 1, which comprises dry mixing the EFI component and the HFI component in the specified weight ratio, or wet mixing the EFI component and the HFI component in the specified weight ratio, optionally followed by isolation of the obtained inulin product in dry form, said isolation step optionally including a spray-drying step.

10. The composition containing an inulin product according to claim 1, and one or more edible or pharmaceutically acceptable components.

11. The composition according to claim 10, wherein the one or more edible or pharmaceutically acceptable components are selected from the group consisting of a sugar, a polyol, an hydrogenated glucose syrup, a maltodextrin, a sweetener, a food ingredient, a feed ingredient, a food additive, a feed additive, a food intermediate, a feed intermediate, a food product, a feed product, an edible liquid, a drink, a bio-available source of a mineral, a pharmaceutically acceptable excipient, a pharmaceutically active substance, a therapeutically active substance, a pharmaceutical composition and a medicament.

12. The composition according to claim 11, wherein the bio-available source of a mineral comprises a source of calcium and/or a source of magnesium and/or a source of iron.

13. Composition according to claim 11, comprising a food, feed, drink, consumer product, functional food, functional feed, pharmaceutical composition or medicament.

14. A method for preparing a composition according to claim 1 comprising mixing an inulin product with one or more edible or pharmaceutically acceptable components, optionally followed by bringing the composition to a desired form.

15. A method for modifying or modulating the bacterial flora composition in the large intestine or in the distal part of the large intestine of humans, mammals or other vertebrates, comprising feeding to said humans, mammals or other vertebrates an effective amount of the composition according to claim 10.

16. A method for providing one or more improved inulin-associated nutritional effects/benefits in humans, mammals or other vertebrates, comprising feeding to said humans, mammals or other vertebrates an effective amount of the composition according to claim 10.

17. A method according to claim 16, wherein said improved inulin-associated nutritional effect/benefit comprises an effect selected from the group consisting of a dietary fibre effect, modulation of gut function, prebiotic action and/or bifidogenicity, increased absorption of minerals, increased absorption of calcium and/or of magnesium and/or of iron, bone mineral density increase, bone mineral content increase, peak bone mass increase, improvement of bone structure, reduction of bone mineral density loss, reduction of loss of bone structure, modulation of lipid metabolism, stimulation of the immune system, and reduction of risk of colon cancer.

18. A method according to claim 16, wherein said improved inulin-associated nutritional effect/benefit comprises reducing bone demineralization or risk of osteoporosis, or treating osteoporosis in humans.

19. A method according to claim 16, wherein said improved inulin-associated nutritional effect/benefit comprises a treatment of a post-menopausal woman or an elderly person.

20. A method according to claim 16, wherein said improved inulin-associated nutritional effect/benefit is for reducing risk of colon cancer, or for treatment of colon cancer.

21. A method according to claim 16, wherein said improved inulin-associated nutritional effect/benefit comprises modifying or modulating the fermentation pattern of inulin in the large intestine or in the distal part of the large intestine of humans, mammals or other vertebrates.

* * * * *